(12) United States Patent
Rasooly et al.

(10) Patent No.: US 9,295,742 B2
(45) Date of Patent: Mar. 29, 2016

(54) SYSTEM AND METHOD FOR DISINFECTING A CATHETER SYSTEM

(71) Applicant: PuraCath Medical, Inc., San Francisco, CA (US)

(72) Inventors: Julia A. Rasooly, San Francisco, CA (US); Barnabas Yik, Pleasanton, CA (US); Matt McLean, San Francisco, CA (US)

(73) Assignee: PuraCath Medical, Inc., San Francisco, CA (US)

( * ) Notice: Subject to any disclaimer, the term of this patent is extended or adjusted under 35 U.S.C. 154(b) by 109 days.

(21) Appl. No.: 13/860,706

(22) Filed: Apr. 11, 2013

(65) Prior Publication Data

US 2013/0303996 A1    Nov. 14, 2013

Related U.S. Application Data (60) Provisional application No. 61/624,849, filed on Apr. 16, 2012.

(51) Int. Cl.
*A61L 2/00*    (2006.01)
*A61L 2/10*    (2006.01)

(52) U.S. Cl.
CPC ............... *A61L 2/10* (2013.01); *A61L 2202/24* (2013.01)

(58) Field of Classification Search
CPC .............................. A61L 2/10; A61L 2202/24
USPC ....................................... 422/24; 250/455.11
See application file for complete search history.

(56) References Cited

U.S. PATENT DOCUMENTS

| | | | |
|---|---|---|---|
| 3,517,669 A | 6/1970 | Buono et al. |
| 3,572,375 A | 3/1971 | Rosenberg |
| 3,626,938 A | 12/1971 | Versaci |
| 3,986,508 A | 10/1976 | Barrington |
| 4,209,013 A | 6/1980 | Alexander et al. |
| 4,232,428 A | 11/1980 | Johansson |
| 4,242,310 A | 12/1980 | Greff et al. |
| 4,256,135 A | 3/1981 | Hannah |
| 4,336,223 A | 6/1982 | Hillman |
| 4,340,052 A | 7/1982 | Dennehey et al. |
| 4,346,704 A | 8/1982 | Kulle |
| 4,412,834 A | 11/1983 | Kulin et al. |
| 4,433,244 A | 2/1984 | Hogan |
| 4,439,188 A | 3/1984 | Dennehey et al. |

(Continued)

FOREIGN PATENT DOCUMENTS

| | | |
|---|---|---|
| EP | 0229786 B1 | 3/1990 |
| EP | 0163811 B1 | 8/1991 |

(Continued)

OTHER PUBLICATIONS

Kermode et al.; U.S. Appl. No. 14/857,522 entitled "Ultraviolet Disinfection Unit," filed Sep. 17, 2015.

(Continued)

*Primary Examiner* — Kevin Joyner
(74) *Attorney, Agent, or Firm* — ShayGlenn LLP (57) ABSTRACT

A system for disinfecting or sterilizing a catheter is provided. A housing includes a chamber having lumens for transmitting one or more UV light sources through the lumens and into a Y-set or a transfer-set. The first UV light source and second UV light source emit UV light into the lumens in order to disinfect or sterilize the Y-set and the transfer-set.

19 Claims, 5 Drawing Sheets

(56) References Cited

U.S. PATENT DOCUMENTS

| | | | |
|---|---|---|---|
| 4,440,207 A | 4/1984 | Genatempo et al. |
| 4,469,835 A | 9/1984 | Laurin |
| 4,473,369 A | 9/1984 | Lueders et al. |
| 4,475,900 A | 10/1984 | Popovich et al. |
| 4,500,788 A | 2/1985 | Kulin et al. |
| 4,503,333 A | 3/1985 | Kulin et al. |
| 4,541,829 A | 9/1985 | Munsch et al. |
| 4,573,980 A | 3/1986 | Karrasch et al. |
| 4,608,472 A | 8/1986 | Kato |
| 4,620,845 A | 11/1986 | Popovich et al. |
| 4,655,762 A | 4/1987 | Rogers |
| 4,745,950 A | 5/1988 | Mathieu |
| 4,774,415 A | 9/1988 | Biegel et al. |
| 4,877,964 A | 10/1989 | Tanaka et al. |
| 4,878,516 A | 11/1989 | Mathieu |
| 4,882,496 A | 11/1989 | Bellotti et al. |
| 4,948,980 A | 8/1990 | Wedekamp |
| 4,949,723 A | 8/1990 | Wallace et al. |
| 4,950,230 A | 8/1990 | Kendell |
| 4,980,374 A | 12/1990 | Steudle et al. |
| 5,047,011 A | 9/1991 | Caron et al. |
| 5,057,074 A | 10/1991 | Suzuki et al. |
| 5,105,853 A | 4/1992 | Lie |
| 5,147,321 A | 9/1992 | Slonina et al. |
| 5,190,534 A | 3/1993 | Kendell |
| 5,221,267 A | 6/1993 | Folden |
| 5,242,150 A | 9/1993 | Shiffler et al. |
| 5,336,173 A | 8/1994 | Folden |
| 5,417,673 A | 5/1995 | Gordon |
| 5,427,135 A | 6/1995 | Kieper |
| 5,536,258 A | 7/1996 | Folden |
| 5,540,668 A | 7/1996 | Wilson et al. |
| 5,603,902 A | 2/1997 | Maltais et al. |
| 5,612,001 A | 3/1997 | Matschke et al. |
| 5,713,850 A | 2/1998 | Heilmann et al. |
| 5,714,119 A | 2/1998 | Kawagoe et al. |
| 5,855,203 A * | 1/1999 | Matter .................... 128/207.14 |
| 6,027,489 A | 2/2000 | Galato |
| 6,120,166 A | 9/2000 | Price |
| 6,228,332 B1 | 5/2001 | Dunn et al. |
| 6,245,570 B1 | 6/2001 | Grimm et al. |
| 6,418,257 B1 | 7/2002 | Nath |
| 6,461,568 B1 | 10/2002 | Eckhardt |
| 6,461,569 B1 | 10/2002 | Boudreaux |
| 6,470,888 B1 | 10/2002 | Matter |
| 6,485,483 B1 | 11/2002 | Fujii |
| 6,569,564 B1 | 5/2003 | Lane |
| 6,592,558 B2 | 7/2003 | Quah |
| 6,682,507 B2 | 1/2004 | Irish |
| 6,696,023 B2 | 2/2004 | Grimm et al. |
| 6,803,363 B2 | 10/2004 | Polaschegg |
| 6,834,984 B2 | 12/2004 | Tausch et al. |
| 7,083,605 B2 | 8/2006 | Miyahara |
| 7,198,611 B2 | 4/2007 | Connell et al. |
| 7,232,428 B1 | 6/2007 | Inukai et al. |
| 7,232,429 B2 | 6/2007 | Moreci |
| 7,274,847 B2 | 9/2007 | Gowda et al. |
| 7,452,346 B2 | 11/2008 | Axelsson |
| 7,497,849 B2 | 3/2009 | Fangrow |
| 7,806,851 B2 | 10/2010 | Cerasoli |
| 7,834,328 B2 | 11/2010 | Redmond et al. |
| 7,955,295 B2 | 6/2011 | Lee et al. |
| 8,197,087 B2 | 6/2012 | Sobue et al. |
| 8,282,829 B2 | 10/2012 | Yu et al. |
| 8,431,074 B2 | 4/2013 | Neer |
| 8,478,385 B2 | 7/2013 | Liu et al. |
| 8,585,681 B2 | 11/2013 | Boenig et al. |
| 8,641,659 B2 | 2/2014 | Soykan et al. |
| 2003/0010927 A1 | 1/2003 | Wedekamp |
| 2003/0017073 A1 | 1/2003 | Eckhardt et al. |
| 2003/0191356 A1* | 10/2003 | Moreci ..................... 600/4 |
| 2005/0013729 A1 | 1/2005 | Brown-Skrobot et al. |
| 2005/0124970 A1 | 6/2005 | Kunin et al. |
| 2005/0163655 A1 | 7/2005 | Lin et al. |
| 2005/0261621 A1 | 11/2005 | Perez |
| 2006/0027270 A1 | 2/2006 | Truitt et al. |
| 2006/0122559 A1 | 6/2006 | Shia et al. |
| 2006/0147339 A1 | 7/2006 | Hunter et al. |
| 2006/0186010 A1* | 8/2006 | Warnack et al. .............. 206/438 |
| 2007/0023710 A1 | 2/2007 | Tom et al. |
| 2007/0179473 A1* | 8/2007 | Masters et al. ................ 604/533 |
| 2007/0232989 A1 | 10/2007 | Kitani et al. |
| 2007/0274879 A1 | 11/2007 | Millikin |
| 2008/0045884 A1 | 2/2008 | Landherr et al. |
| 2008/0183126 A1 | 7/2008 | Landherr et al. |
| 2008/0183127 A1 | 7/2008 | Landherr et al. |
| 2008/0195031 A1 | 8/2008 | Kitani et al. |
| 2008/0306454 A1 | 12/2008 | Sikora |
| 2009/0012451 A1 | 1/2009 | Sobue et al. |
| 2009/0012459 A1 | 1/2009 | Sobue et al. |
| 2009/0149776 A1 | 6/2009 | Adams |
| 2009/0205664 A1 | 8/2009 | Lyon |
| 2009/0257910 A1 | 10/2009 | Segal |
| 2009/0259203 A1 | 10/2009 | Hu et al. |
| 2009/0289015 A1 | 11/2009 | Levy |
| 2009/0320316 A1 | 12/2009 | Zakai |
| 2010/0072506 A1* | 3/2010 | Bae et al. ......................... 257/99 |
| 2010/0249586 A1 | 9/2010 | Cocker et al. |
| 2011/0064608 A1 | 3/2011 | Lee et al. |
| 2011/0085936 A1 | 4/2011 | Haytman et al. |
| 2011/0165020 A1 | 7/2011 | Tryggvason et al. |
| 2011/0213339 A1 | 9/2011 | Bak |
| 2012/0053512 A1 | 3/2012 | Muse |
| 2012/0161032 A1 | 6/2012 | Arcand et al. |
| 2012/0205825 A1 | 8/2012 | Nagafuji et al. |
| 2012/0321509 A1* | 12/2012 | Bak ................................ 422/24 |
| 2013/0323119 A1 | 12/2013 | Alwan |
| 2014/0334974 A1 | 11/2014 | Rasooly et al. |

FOREIGN PATENT DOCUMENTS

| | | |
|---|---|---|
| FR | 2799373 | 4/2001 |
| JP | 2008/68049 | 3/2008 |
| WO | WO92/19284 A1 | 11/1992 |
| WO | WO2007/103998 A2 | 9/2007 |
| WO | WO2008/014437 A2 | 1/2008 |
| WO | WO2009/094034 A1 | 7/2009 |
| WO | WO2011/000787 | 1/2011 |
| WO | WO2011/143140 A2 | 11/2011 |

OTHER PUBLICATIONS

Murphy-Chutorian et al.; U.S. Appl. No. 14/731,110 entitled; "Transfer Catheter for Ultraviolet Disinfection," filed Jun. 4, 2015.

Bak et al.; Disinfection of pseudomonas aeruginosa biofilm contaminated tube lumens with ultraviolet C light emitting diodes; Biofouling: The Journal of Bioadhesion and Biofilm Research; 26(1); pp. 31-38; Jan. 2010.

Bak et al.; Dose requirement for UVC disinfection of catheter biofilms; Biofouling: The Journal of Bioadhesion and Biofilm Research; 25(3); pp. 289-296; Apr. 2009.

Bak et al.; Potential in vivo UVC disinfection of catheter lumens: estimation of the doses received by the blood flow outside the catheter tip hole; Photochemistry and Photobiology; 87(2); pp. 350-356; Mar.-Apr. 2011.

Bak et al.; UVC fluencies of preventative treatment of pseudomonas aeruginosa contaminated polymer tubes; Biofouling: The Journal of Bioadhesion and Biofilm Research; 26(7); pp. 821-828; Oct. 2010.

Qamar et al; Clinical outcomes in peritoneal dialysis: Impact of continuous improvement quality initiatives; Advances in Peritoneal Dialysis; vol. 25; pp. 76-79; 2009 (year of pub. sufficiently earlier than effective US filed and any foreign priority date).

* cited by examiner

SYSTEM AND METHOD FOR DISINFECTING A CATHETER SYSTEM

BACKGROUND OF THE INVENTION

Peritoneal dialysis (PD) is a treatment for patients with chronic kidney disease. In PD, the peritoneum in the abdomen of a dialysis patient acts as a membrane across which fluids and dissolved substances are exchanged with blood. Dialysate solution enters the abdomen through an access site implemented as a permanent catheter tube, and after some time (e.g., a few hours), the dialysate becomes saturated with waste and is eventually drained through the catheter and out to a drain bag. PD patients typically perform dialysis themselves, in a regular exchange throughout the day (known as Continuous Ambulatory Peritoneal Dialysis, or CAPD) and/or overnight (known as Continuous Cyclic Peritoneal Dialysis, or CCPD) while the patient is asleep.

There are typically three components in a system for PD, including an indwelling catheter surgically implanted in the abdomen of the patient, disposable tubing (typically "Y-set" tubing) that transfers fresh dialysate solution from a dialysate source (and/or saturated waste fluid to a drain bag), and an extension catheter (sometimes referred to as the transfer set) that connects the indwelling catheter to the Y-set. Since the extension catheter is the primary connection site and typically includes an open port via a luer lock, the extension catheter is frequently exposed to the external environment and therefore is at an elevated risk of contamination. Standard conventional protocol for disinfection during PD, which includes numerous steps, is complicated and lacks full patient compliance. For at least these reasons, a patient undergoing PD is highly susceptible to infection that may lead to sepsis or other health complications.

Thus, there is a need in the medical field to create a new and useful system and method for disinfecting or sterilizing a catheter system. This invention provides such a new and useful system and method.

SUMMARY OF THE INVENTION

A system is provided to disinfect or sterilize a catheter system for a patient undergoing peritoneal dialysis (PD), although the system can also be used to disinfect or sterilize any suitable catheter system or other fluid channel.

In one embodiment, a system for disinfecting or sterilizing a catheter includes a housing having a chamber and a first lumen and a second lumen that are orthogonal to each other. A first UV light source is attached to the chamber in order to emit UV light into the first lumen. A second UV light source is attached to the chamber to emit UV light into the second lumen. A Y-set, which is known in the art, is attached to the housing so that the Y-set is aligned with the first lumen. A transfer-set, also known in the art, extends from the patient and is attached to the housing so that the transfer-set is aligned with the second lumen. The first UV light source emits UV light into the first lumen and into the Y-set and the second UV light source emits UV light into the second lumen and into the transfer-set, thereby disinfecting or sterilizing the Y-set and the transfer-set.

DETAILED DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
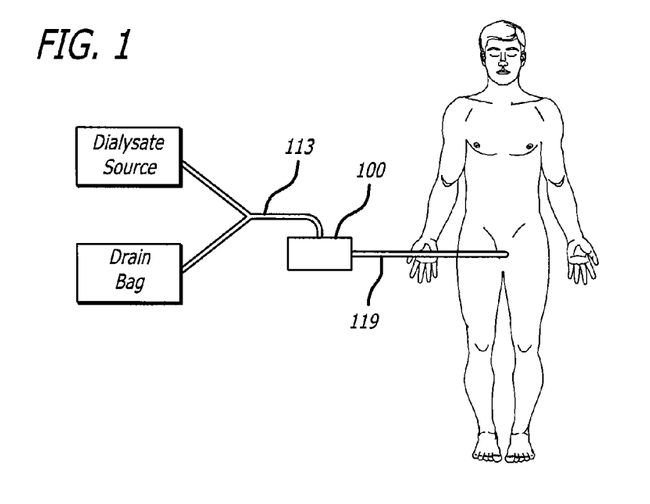
FIG. 1 is a schematic of the system relative to a peritoneal dialysis setup for a patient.
Figure 2:
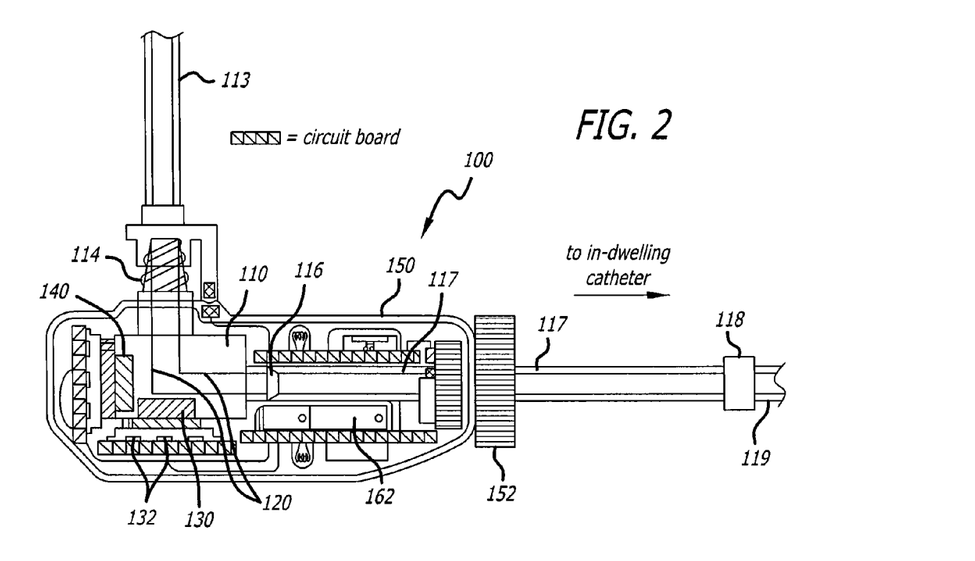
FIG. 2 is a plan view, partially in cross-section, depicting the Y-set and the transfer-set connected to the housing and chamber.
Figures 3, 4:
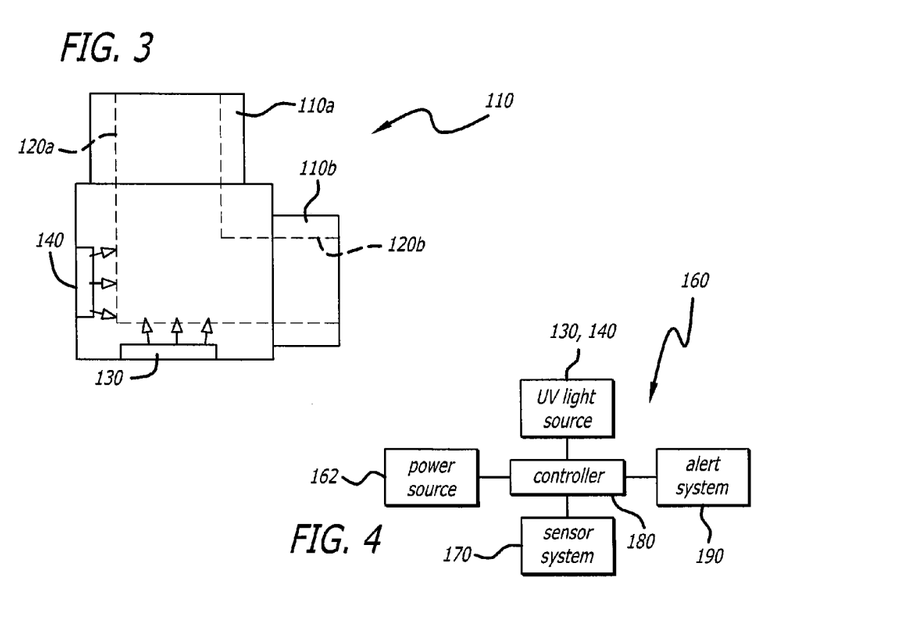
FIG. 3 is a schematic depicting the first lumen and the second lumen at right angles to each other inside the chamber.
FIG. 4 depicts a flow chart of one embodiment of the controller operating the various systems including the power source, UV light sources, alert system, and sensor system.

As shown in FIG. 1, a preferred system 100 can preferably be used to disinfect or sterilize a catheter system for a patient undergoing peritoneal dialysis (PD), although the system 100 can additionally or alternatively be used to disinfect or sterilize any suitable catheter system or other fluidic channel. As shown in FIGS. 2 and 3, a preferred system 100 for disinfecting a catheter system includes: a chamber 110 defining a lumen 120 including a first lumen segment 120a and a second lumen segment 120b approximately orthogonal to the first lumen segment 120a; a first light source 130 coupled to the chamber 110 and configured to emit ultraviolet light along the first lumen segment 120a; and a second light source 140 coupled to the chamber 110 and configured to emit ultraviolet light along the second lumen segment 120b. The emitted ultraviolet light preferably disinfects the lumen 120 and/or a connection site at each end of the lumen (e.g., resulting in at least a 2 log microbial reduction). The emitted light can additionally or alternatively result in any suitable level of microbial reduction, such as sterilization (e.g., at least a 6 log microbial reduction). At least one of the lumen segments 120a, 120b is preferably configured to fluidically communicate with connected to an external fluid source and/or bag, and the other of the lumen segments 120a, 120b is preferably configured to fluidically communicate with an indwelling catheter implanted in a peritoneal dialysis patient. However, the lumen segments 120a, 120b in the chamber 110 can be coupled to any suitable fluidic channels to disinfect or sterilize the connection sites of transfer for any suitable fluid or other object placed within the lumen.

The chamber 110 preferably functions to provide a disinfectable or sterilizable connection point between an external fluid source and a catheter implanted in a patient. As shown in FIGS. 2 and 3, the chamber 110 preferably defines a lumen 120 through which fluid (e.g., dialysate) flows. In a preferred embodiment of the system 100, the lumen 120 is preferably approximately four millimeters in diameter and has an approximately circular cross-section, corresponding to the diameter and shape of conventional PD, but can alternatively be of any suitable size and geometrical shape.

As shown in FIG. 3, the chamber 110 and chamber lumen 120 preferably each includes at least two segments arranged at a non-zero angle relative to one another. In particular, the chamber 110 preferably includes a first chamber segment 110a defining a first lumen segment 120a, and a second chamber segment 110b defining a second lumen segment 120b. The second chamber segment 110b is preferably approximately orthogonal to the first chamber segment 110a, and the second lumen segment 120b is preferably approximately orthogonal to the first lumen segment 120a. However, the chamber 110 can include any suitable number of chamber segments 110a, 110b arranged in any suitable relative angle, and the lumen 120 can include any suitable number of lumen segments 120a, 120b arranged in any suitable relative angle. The ultraviolet (UV) light sources 130 and 140 are preferably mounted to an outer surface of the chamber 110 such that each light source 130, 140 radiates UV light through the chamber wall and along a respective lumen segment 120a, 120b. In the preferred orthogonal chamber arrangement, the light sources 130, 140 can disinfect or sterilize a substantial portion of the lumen 120 without physically interfering with the lumen 120 and fluid passing through the lumen.

The first chamber segment 110a is preferably configured to couple to a Y-set 113 (or other suitable tubing) that can be connected to a dialysate bag and/or a drain bag. As used herein, the Y-set 113 can include a connector and/or tubing, and also can be referred to broadly as a first connector. The second chamber segment 110b is preferably configured to couple to an indwelling catheter 119 in a PD patient. As shown in FIG. 2, in one preferred embodiment, the first chamber segment 110a can include a male luer lock connection 114 configured to couple to conventional Y-set 113, and the second chamber segment 110b includes a barbed tube fitting 116 configured to couple to conventional PD 117, sometimes referred to as a transfer-set 117, which preferably leads to a female luer lock 118. As used herein, the transfer set 117 can include a connector and/or tubing, and also can be referred to broadly as a second connector. However, the first and/or second chamber segments 110a and 110b can include any suitable mating feature to couple to tubing, such as threads, or can couple to any suitable tubing adapter.

In one example implementation of the preferred system 100, the chamber 110 is composed of an UV light-transmissive material, such as Topas® High UV-Grade Cyclic Olefin Copolymer. Other light-transmissive materials include cyclic olefin copolymer (COC), polymethylpentene (PMP), UVT polymethymethylacrylate (PMMA), perfluoroalkoxy (PFA), fluorinated ethylene propylene (FEP), terpolymer (THV). The chamber 110 is preferably injection molded, but can alternatively be machined by three-dimensional printing, milling, or any suitable manufacturing process. In the preferred system 100, the chamber 110 has a smooth surface finish (e.g., from an injection molding manufacturing process, and/or a suitable polishing or smoothing process) that can result in less UV reflection and/or refraction, and thereby result in better light transmission from the UV light sources into the lumen 120. However, the chamber no can have any suitable kind, type, or quality of surface.

The first and second light sources 130 and 140 preferably function to disinfect or sterilize at least a portion of the lumen 120 and/or connection sites at an end of the lumen. As shown in FIGS. 2 and 3, each light source preferably emits UV light along a respective lumen segment and/or connection site at an end of the lumen 120 (e.g., where the chamber 110 connects to Y-set 113 or to transfer-set 117). The first and second light sources 130 and 140 are preferably coupled to an outer surface of the chamber 110, and oriented such that they emit UV light through a wall of the chamber 110. The preferred system 100 can include more than two light sources coupled to the chamber 110. For example, the preferred system 100 can include third and fourth light sources (not shown) coupled proximate to the connection site ends of the chamber 110 (e.g., at the Y-set end and/or the transfer-set end of the chamber). In this example, the third and fourth light sources are preferably configured to emit UV light along the lumen segments toward the orthogonal juncture of the chamber 110, traveling in directions approximately opposite to light emitted by the first and second light sources. However, the preferred system 100 can include any suitable number of light sources. Furthermore, the preferred system 100 can include mirrors, lenses, reflectors, emitters, and/or any other suitable optical elements within the chamber 110 that reflect, refract, focus, disperse, and/or manage UV light from the UV light sources, thereby increasing UV light distribution, intensity, and/or area/efficacy of disinfection or sterilization.

The light sources 130 and 140 can be coupled to the chamber 110 in one or more of several variations. In a first variation, the light sources 130 and 140 are located in slots located on the chamber 110. In a second variation, the light sources 130 and 140 are coupled to the chamber 110 with a fastener such as mechanical fasteners or adhesives. In a third variation, the light sources 130 and 140 are fit into a mating surface, such as through a snap fit or press fit. Furthermore, the light sources 130 and 140 can be coupled to the chamber 110 with suitable alignment features (e.g., keys) to help ensure a particular orientation of the light sources. However, the light sources 130 and 140 can be coupled to the chamber 110 in any suitable manner.

In another variation of the preferred system 100, the light sources 130 and 140 are preferably UV LEDs. In an example implementation of the preferred system 100, the light sources 130 and 140 are UVClean LEDs manufactured by Sensor Electronic Technology, custom manufactured to include four UV diodes in a single TO-39 housing. However, the light sources can be any suitable UV LED, or any suitable UV-emitting source (e.g., lamp, bulb). The light sources 130 and 140 can be configured to radiate UV light continuously for a predetermined period of time (e.g., two minutes) or can intermittently radiate in pulses of high power output in pulse width modulation.

As shown in FIG. 2, the preferred system 100 can include one or more heat sinks 132 to dissipate heat generated by the light sources 130 and 140. The heat sinks are preferably coupled to one or more of the light sources 130 and 140 and made of a suitably thermally conductive material (e.g., aluminum, aluminum alloy, and the like). The heat sinks 132 can include fins for increased cooling by convection. Alternatively, the preferred system 100 can include other suitable passive or active means for dissipating or redirecting heat generated by the light sources 130 and 140, such as heat pipes or fans.

As shown in FIG. 2, the preferred system 100 further includes a housing 150 that substantially encloses the chamber 110 and preferably functions to protect the chamber 110, light sources 130 and 140, and other components of the system. The housing 150 is preferably made of a material that includes a UV light opaque material. At least a portion of the housing material can be translucent or transparent with regard to visible light (and/or include apertures), to enable a user to visualize at least some components, such as indicator lights, located within the housing. The housing 150 is preferably formed by injection molding, but can additionally or alternatively be formed by any suitable manufacturing process. The housing 150 in the preferred system 100 can further include a drain valve 152 that controls fluid flow from the transfer-set 117 to the Y-set 113. The drain valve 152 can be actively controlled or passively controlled to an open or closed state. Alternatively, the drain valve 152 can be coupled to the second chamber segment 110b.

Figure 5:
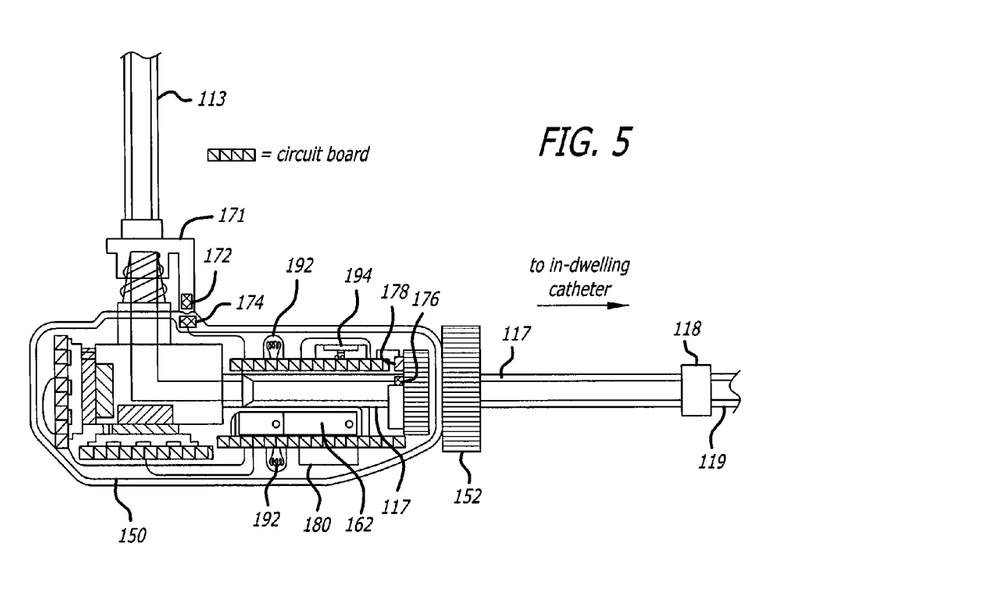
FIG. 5 is a plan view, partially in cross-section, depicting one embodiment of the system in which the Y-set and the transfer-set are connected to the housing and chamber.

As shown in FIGS. 4 and 5, the preferred system 100 further includes an electronic subsystem 160 including a power source 162 configured to power the electronic subsystem 160 and light sources 130 and 140, a sensor system 170 configured to indicate isolation (or quarantine) of the chamber 110 from the external embodiment, a controller 180 configured to activate the first and second light sources 130 and 140 based on the indications of the sensor system 170, and/or an alert system 190 configured to indicate disinfection or sterilization status.

The power source 162 of the preferred system 100 preferably functions to power the electronic subsystem 160 and/or the light sources 130 and 140. As shown in FIG. 5, the power source 162 preferably includes a battery, which can be located within the housing 150 outside the chamber 110, or in any suitable location. The power source 162 can additionally or alternatively include any suitable external power source.

The sensor system 170 of the preferred system 100 preferably functions to indicate connection of external tubing (e.g., Y-set 113 and transfer-set 117) to one or more ends of the chamber and drain valve closure, and/or to indicate sufficient isolation of the chamber from the external environment for disinfection or sterilization. In a preferred embodiment of the system 100, the sensor system 170 can include one or more Hall effect sensors. As shown in FIG. 5, the preferred system 100 can include a Hall effect sensor 174 that is adjacent to the connection site of the first chamber segment 110a (near an external surface of the housing 150) and that cooperates with a magnet 172 located on the Y-set 113 to signal connection between the chamber 110 and the Y-set. For example, the magnet 172 can be on a neodymium magnet on a collar or other fitting 171 coupled to the Y-set (e.g., on the female luer-lock connector on conventional Y-set). When the magnet 172 on the Y-set is in sufficient proximity to the Hall effect sensor 174 on the chamber, the Hall effect sensor 174 preferably outputs an electronic signal (e.g., absolute or relative voltage) that can be used as a switch to signal connection between the chamber and the Y-set. Additionally or alternatively, the sensor system 170 preferably further includes a second Hall effect sensor 178 that cooperates with a magnet 176 coupled to the drain valve 152 (or alternatively, the second Hall effect sensor can be coupled to the drain valve 152 and magnet can be located on a nearby portion of the chamber) to signal that the drain valve 152 is in the closed state. When the drain valve 152 is closed, the magnet 176 on the drain valve 152 is preferably sufficiently proximate to the second Hall effect sensor 178 to induce the second Hall effect sensor 178 to output an electronic signal, such that the second Hall effect sensor 178 can be used as a switch to signal closure of drain valve 152. In an alternative variation of the sensor system 170, the sensor system 170 can include physical switches (e.g., electrical contact touch surfaces forming selectively complete electrical circuits, buttons) on the Y-set, chamber segment ends, and/or drain valve 152 that indicate connection of the chamber to the Y-set and/or drain valve closure. However, the sensor system 170 can include any suitable sensors and/or switches.

The controller 180 of the preferred system 100 preferably functions to activate the first and second light sources 130 and 140 based on the indications of the sensor system 170. When the sensor system 170 indicates isolation of the chamber 110 for a sufficient period of time (e.g., verification period of approximately one second), the controller 180 preferably activates the light sources 130 and 140 to emit UV light for disinfection or sterilization of the chamber 110. In a preferred embodiment, the controller 180 preferably configured the light sources 130 and 140 to emit UV light for approximately two minutes per disinfection cycle (continuously or intermittently in pulse width modulation), but can alternatively configure the light sources 130 and 140 to emit UV light in any suitable manner. If, at any point during the disinfection cycle, the signals from the sensor system 170 indicate disconnection from the Y-set 113 and/or opening of the drain valve 152 (or other breach in chamber isolation or other suitable fault), the controller 180 can deactivate the light sources 130 and 140, thereby halting the disinfection cycle. The controller 180 can communicate any such faults through the alert system 190 or suitable interface or display.

In a preferred embodiment, the controller 180 in the preferred system 100 can further optimize components of the electronic subsystem 160, such as in power consumption and other operational aspects. For example, the controller 180 can use sampled voltages in feedback to monitor overall power status (e.g., battery charge level) and/or performance of the battery 162 and/or charge pumps used to power the light sources 130 and 140. Such feedback can be used to diagnose degradation of the light sources 130 and 140 or other electrical components. Furthermore, the controller 180 in the preferred system 100 can establish a "sleep" mode in which power consumption is placed at a minimum to extend battery life; this sleep mode can be interrupted by, for example, activation of the sensor system 170 indicating connection to Y-set 113.

The alert system 190 of the preferred system 100 preferably functions to indicate to a user the status of the disinfection cycle. As shown in FIG. 5, in a preferred embodiment, the alert system 190 includes LEDs 192 coupled to the housing 150. For example, the alert system 190 can include one or more green LEDs that indicate proper operation of the disinfection cycle, and one or more red LEDs that indicate any faults or errors in the disinfection cycle. In an example for illustrative purposes only, a green LED is activated to indicate successful connection of the chamber to the Y-set and drain valve closure, and blinks throughout the disinfection cycle to indicate that the disinfection cycle is in progress. When the disinfection cycle is complete, the green LED can be lit continuously to indicate to a user that the disinfection cycle is finished. However, any suitable number of LEDs 192 can be any suitable color and flash in any suitable manner. In this illustrative example, the red LED can be activated to indicate any error or fault during the disinfection cycle. In some variations of the preferred alert system 190, the alert system 190 can additionally or alternatively include components 194 providing audible alerts (e.g., musical tones or beeps), and/or text messages on the housing 150 or a display console to indicate various stages and/or completion of the disinfection cycle.

Figure 6:
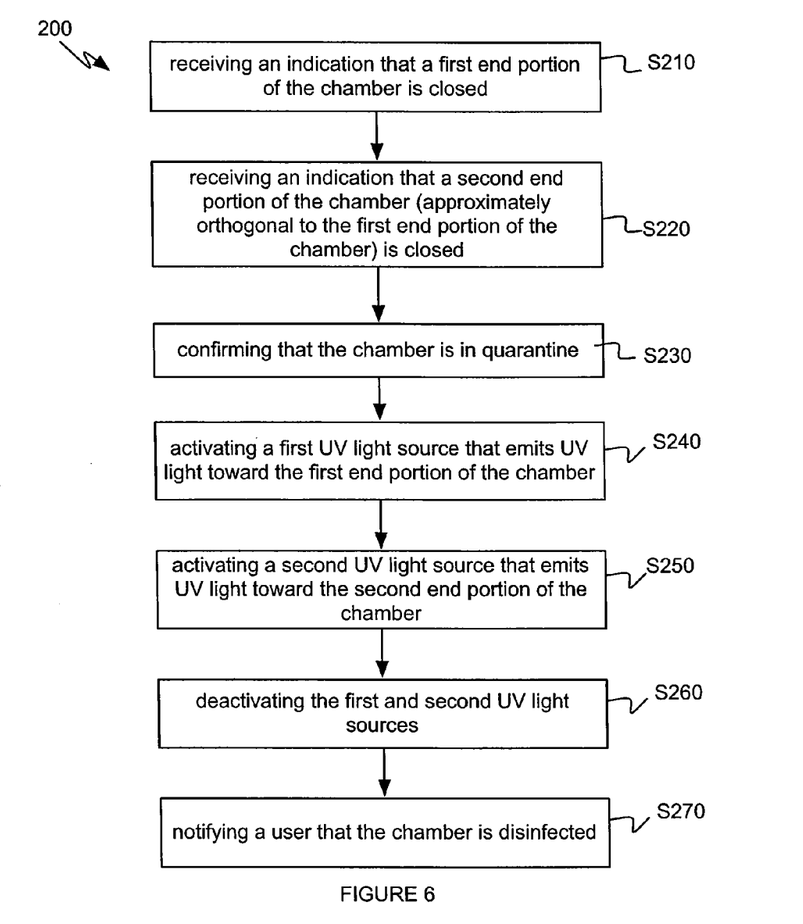
FIG. 6 is flow chart depicting the operation of the sensors during activation of the UV light source.

As shown in FIG. 6, a preferred method 200 of disinfecting or sterilizing a chamber in a transfer set of a catheter system for peritoneal dialysis includes: receiving an indication that a first end portion of the chamber is closed in block S210; receiving an indication that a second end portion of the chamber, approximately orthogonal to the first end portion of the chamber, is closed in block S220; confirming that the chamber is in isolation in block S230; in a disinfection cycle, while the chamber is in isolation, activating a first ultraviolet light source that emits ultraviolet light toward the first end portion of the chamber in block S240 and activating a second ultraviolet light source that emits ultraviolet light toward the second end portion of the chamber in block S250; and, if the chamber becomes not isolated or when the disinfection cycle is complete, deactivating the first and second ultraviolet light sources in block S260. The method 200 can further include notifying a user that the chamber is disinfected in block S270. Although FIG. 6 describes the method in terms of disinfection, the method can additionally or alternatively be used for sterilization or any suitable level of microbial reduction.

Figure 7A:
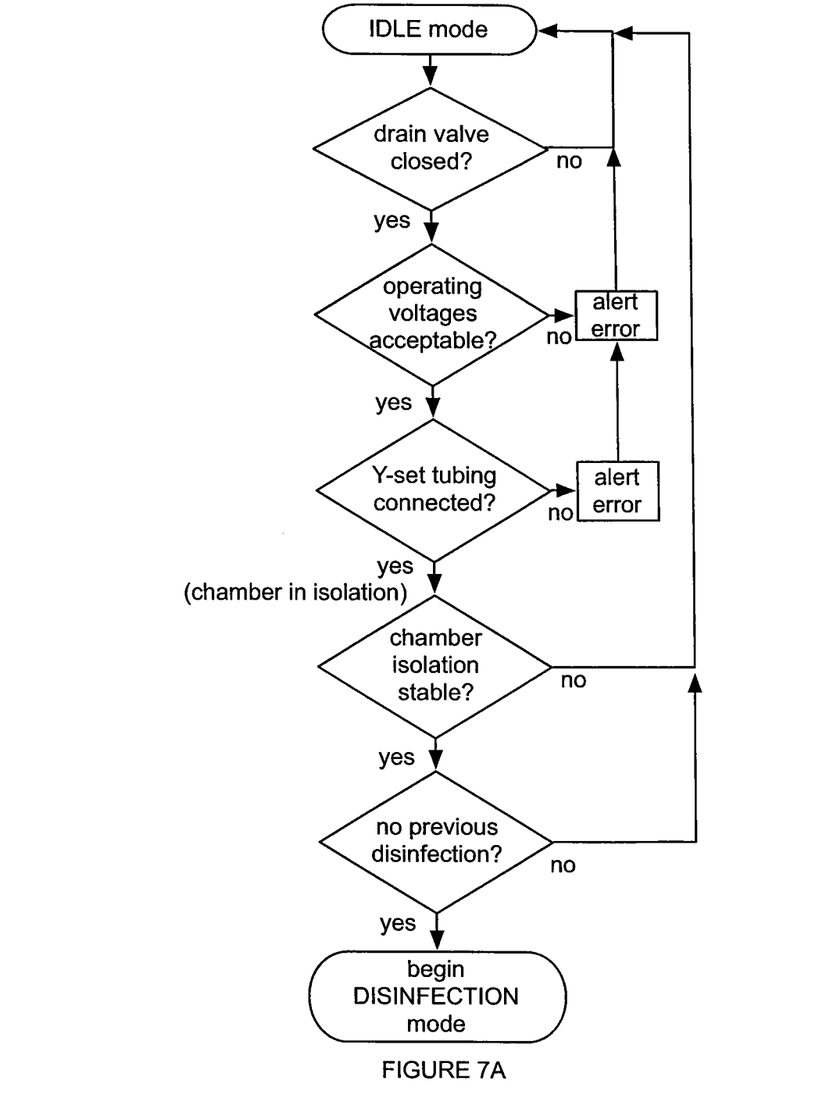
FIG. 7A is a flow chart summarizing the verification processes performed to transition between an IDLE mode and a DISINFECTION mode.
Figure 7B:
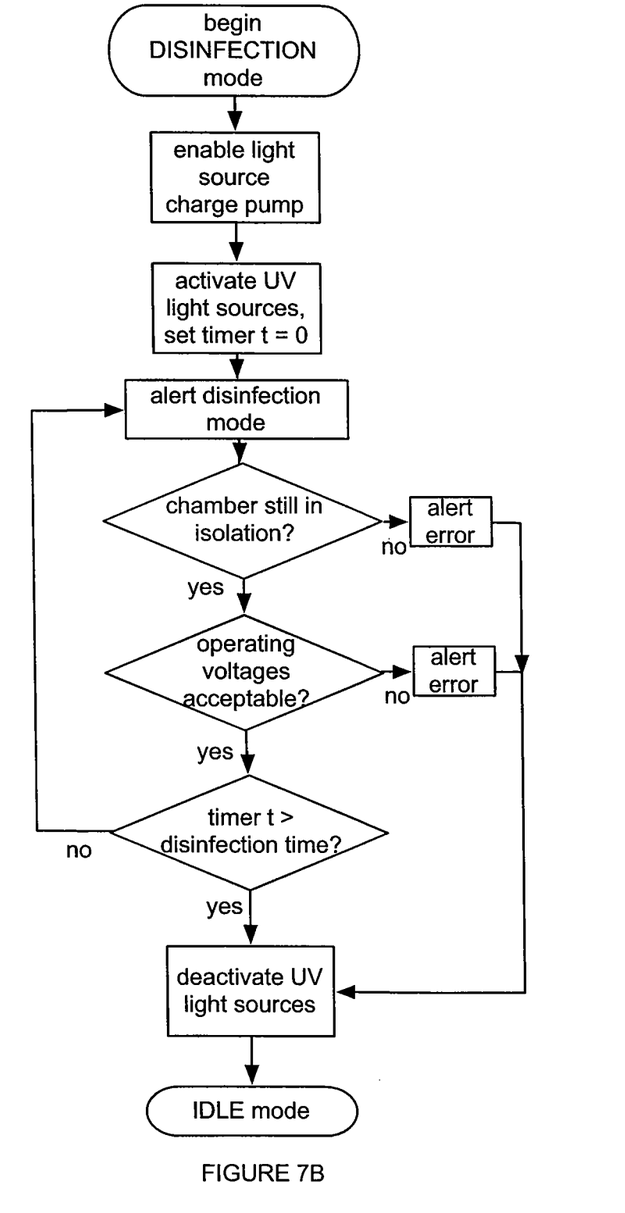
FIG. 7B is a flow chart summarizing the verification processes performed to transition between a DISINFECTION mode and an IDLE mode.

Additional operational steps in the preferred method 200, which can be performed with the preferred system described above or with any suitable system, are summarized in FIGS. 7A and 7B. In particular, FIG. 7A summarizes verification processes performed to transition between an IDLE mode and a DISINFECTION mode, and FIG. 7B summarizes disinfection and verification processes performed to transition between the DISINFECTION mode and the IDLE mode. Although FIGS. 7A and 7B describe the method in terms of disinfection, the method can additionally or alternatively be used for sterilization or any suitable level of microbial reduction.

The system 100 and method 200 of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the controller 180. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

What is claimed:

1. A system for disinfecting or sterilizing a catheter, comprising:
    a housing having a chamber, a first lumen extending in the chamber in a direction substantially orthogonal to a second lumen in the chamber;
    a first UV light source attached to the chamber and a second UV light source attached to the chamber, the first UV light source positioned in the chamber to emit UV light into the first lumen and the second UV light source positioned in the chamber to emit UV light into the second lumen;
    a Y-set attached to the housing so that the Y-set is aligned with the first lumen;
    a transfer-set from the patient attached to the housing so that the transfer-set is aligned with the second lumen;
    the first UV light source emits UV light into the first lumen and the Y-set and the second UV light source emits UV light into the second lumen and the transfer-set thereby disinfecting or sterilizing the Y-set and the transfer-set; and
    wherein a sensor system indicates connection of the Y-set and the transfer-set and a Hall effect sensor indicates when a drain valve is open or closed.

2. The system of claim 1, wherein a Hall effect sensor indicates the connection between the chamber and the Y-set.

3. The system of claim 1, wherein an electronic controller activates and deactivates the first UV light source and the second UV light source.

4. The system of claim 1, wherein a power source is mounted in the housing to provide electrical power to the first UV light source and the second UV light source.

5. The system of claim 4, wherein the power source includes at least one battery.

6. The system of claim 1, wherein a power source external to the housing provides electrical power to the first UV light source and the second UV light source.

7. The system of claim 1, wherein the Y-set and the transfer-set are formed of a material that is UV light-transmissive.

8. The system of claim 7, wherein the UV light-transmissive material is a polymer taken from the group of polymers including cyclic olefin copolymer, polymethylpentene, UVT polymethymethylacrylate, perfluoroalkoxy, fluorinated ethylene propylene and terpolymer.

9. The system of claim 1, wherein the first UV light source and the second UV light source is a low-pressure mercury vapor lamp emitting about 86% of UV light at 254 nm.

10. The system of claim 1, wherein an alert system indicates when the first UV light source and the second UV light source are emitting UV light in the chamber.

11. The system of claim 1, wherein the chamber is formed from a UV light-transmissive material.

12. The system of claim 1, wherein the UV light source is one or more light emitting diodes or pulsed light white.

13. The system of claim 1, wherein one or more mirrors are positioned in the chamber to direct the UV light source.

14. The system of claim 1, wherein one or more lenses are positioned in the chamber to manage UV light from the UV light source.

15. The system of claim 1, wherein the housing is permanently attached to the transfer-set.

16. The system of claim 1, wherein the UV light is pulsed using pulse width modulation.

17. The system of claim 1, wherein the housing contains one or more heat sinks to dissipate heat generated by the UV light source.

18. The system of claim 1, wherein the system includes an electronic controller to automatically activate the first UV light source and the second UV light source after a sensor confirms the Y-set is attached to the housing.

19. The system of claim 1, wherein a sensor is configured to operate an alert system to indicate disinfection or sterilization status.

* * * * *